(12) United States Patent
Ruan et al.

(10) Patent No.: US 6,951,645 B2
(45) Date of Patent: Oct. 4, 2005

(54) MONOCLONAL ANTIBODIES RECOGNIZING HUMAN PLATELET MEMBRANE GLYCOPROTEINS AND USE THEREOF IN ANTI-THROMBOTIC THERAPY

(76) Inventors: Changgeng Ruan, 1 San Duo Ziang, Jia-An Bie-Yuan, Apt. 11-202, Suzhou 215002 (CN); George Qingwei Ye, Skyport Corporate Centre, 2355 Derry Road East, Unit 23, Mississauga, Ontario (CA), L5S 1V6

(*) Notice: Subject to any disclaimer, the term of this patent is extended or adjusted under 35 U.S.C. 154(b) by 0 days.

(21) Appl. No.: 10/622,231

(22) Filed: Jul. 17, 2003

(65) Prior Publication Data

US 2004/0013666 A1 Jan. 22, 2004

(51) Int. Cl.⁷ ...................... A61K 39/395; C07K 16/28; C12N 5/20; C12P 21/08
(52) U.S. Cl. ................ 424/143.1; 424/133.1; 424/152.1; 424/153.1; 435/70.21; 435/452; 435/328; 435/334; 435/343; 530/387.3; 530/388.22; 530/388.7
(58) Field of Search ............ 424/133.1, 135.1, 424/141.1, 143.1, 152.1, 153.1; 435/70.21, 452, 328, 334, 343; 436/548; 530/388.22, 388.7, 387.3

(56) References Cited

U.S. PATENT DOCUMENTS

| | | | |
|---|---|---|---|
| 5,387,413 A | * | 2/1995 | Coller ...................... 424/153.1 |
| 5,770,198 A | * | 6/1998 | Coller et al. ............. 424/153.1 |
| 5,777,085 A | * | 7/1998 | Co et al. ............... 530/388.23 |

FOREIGN PATENT DOCUMENTS

CA 1297816 3/1992

EP 557535 B1 12/1997

OTHER PUBLICATIONS

Becker, Richard C., *Thrombin Antagonists and Antiplatelet Agents*, Am J Cardiol 1932;69:39A–51A.

Coller, Barry S., *Progress in Hemostasis and Thrombosis*, 1989; vol. 9:117–124.

Knight, David M., et al, *The Immunogenicity of the 7E3 Murine Monoclonal FAB Antibody Fragment Variable Region is Dramatically Reduced in Humans by Substitution of Human for Murine Constant Regions*, Molecular Immunology, vol. 32, No. 16, pp. 1271–1281, 1995.

Verstraete, Marc, *Synthetic Inhibitors of Platelet Glycoprotein IIb/IIIa In Clinical Development*, Circulation, 2000;102:e76–e80

Changgeng, Ruan, *Monoclonal Antibodies and Thrombotic Diseases*, Science and Technology at the Frontier in China, [Ed. By Chinese Engineering Academy] 2001; vol. 4: 131–145.

Coller, Barry S., et al, *A Murine Monocional Antibody That Completely Blocks the Binding of Fibrinogen to Platelets Produces a Thrombasthenic–like State in Normal Platelets and Binds to Glycoproteins lib and/or IIIa*, J. Clin.Invest. 1983; vol. 72(1):325–338.

* cited by examiner

Primary Examiner—Christopher L. Chin
Assistant Examiner—James L. Grun
(74) Attorney, Agent, or Firm—Thorpe North & Western, LLP

(57) ABSTRACT

A "cocktail" combination of two monoclonal antibodies respectively acting on different sites of the platelet GPIIb-IIIa complex has been disclosed. This "cocktail" combination can completely block receptor function of the GPIIb-IIIa complex, inhibit platelet aggregation and thereby efficiently inhibit thrombosis.

7 Claims, 7 Drawing Sheets

Marker

■ —116,000
● —80,000

■ —51,800

◀ —34,700
● —30,000

— ● —20,000

Y262

Marker

MONOCLONAL ANTIBODIES RECOGNIZING HUMAN PLATELET MEMBRANE GLYCOPROTEINS AND USE THEREOF IN ANTI-THROMBOTIC THERAPY

This application claims priority to Chinese Patent Application No. 02125227.0, filed on Jul. 17, 2002.

BACKGROUND OF THE INVENTION

1. Field of the Invention

The present invention relates to the field of medical immunology and more particularly to monoclonal antibodies that can recognize platelet membrane glycoproteins and hybridomas for producing the monoclonal antibodies. The present invention also provides anti-platelet compositions containing said monoclonal antibodies and uses thereof in anti-thrombotic therapy.

2. Related Art

Diseases induced or complicated by thrombus formation seriously threaten human health and are one of the most common reasons for human death. Accordingly, prevention of thrombus formation has become a highlight in modern medical research. Platelets, as a major component of thrombi, play a critical role in thrombosis. In normal blood circulation platelets exist in a resting state, but when the blood vessel is damaged and the subendothelial matrix, such as collagen, is exposed, platelets will adhere to the subendothelial matrix of the damaged vessel via direct binding of membrane glycoproteins thereof to plasma adhesive proteins such as von Willebrand factor (vWF). The platelets that adhere to the matrix or are activated by some agonist produced in the process of blood coagulation and tissue injury will change their form, spread their pseudopodia and further release intracellular granular contents. Concurrently, the platelet membrane glycoprotein (GP) IIb-IIIa complex is activated to form a receptor for adhesive molecules, the binding of fibrinogen to which then promotes adhesion and aggregation of platelets and ultimately leads to the formation of a platelet thrombus at the damaged vessel wall (Plow E. F, Ginsberg M. H. Cellular adhesion: GPIIb/IIIa as a prototypic adhesion receptor. *Progress in Haemostasis and Thrombosis*. 1989; 9: 117–124). Platelet thrombosis plays a key role in the pathogenesis of diseases associated with arterial thrombo-embolism, including coronary thrombosis such as occurs during acute myocardial infarction. Consequently, anti-platelet agents have become important therapy for diseases of arterial thrombo-embolism including coronary heart disease (Becker R. C. Thrombin antagonists and antiplatelet agents. *Am J Cardiol* 1992; 69: 39E; Ruan C. G. Monoclonal antibodies and thrombotic diseases. *Science and Technology at the Frontier in China* [Ed. By Chinese Engineering Academy] 2001;Vol 4: 131–145). Drugs currently utilized in clinics include Aspirin, Dipyridamole and Ticlopidine etc., which only function at one of the steps in the process of platelet activation and their curative effects are not as good as those of GPIIb-IIIa antagonists. GPIIb-IIIa antagonists directly inhibit the binding of fibrinogen to the GPIIb-IIIa complex receptor, the final common pathway of platelet aggregation, and then inhibit the formation of a platelet thrombus, and accordingly have become specific and potent anti-platelet agents and exhibit favorable prospects for application in diseases associated with thrombosis. There are three kinds of GPIIb-IIIa antagonists: monoclonal antibodies such as c7E3, synthetic peptides such as Eptifibatide, and non-peptide small molecules such as Tirofiban (Ruan C. G. Monoclonal antibodies and thrombotic diseases. *Science and Technology at the Frontier in China* [Ed. By Chinese Engineering Academy] 2001;Vol 4: 131–145. Verstraete M. Synthetic inhibitors of platelet GPIIb/IIIa in clinical development. *Circulation.* 2000; 101(6): 76–80).

The technique of producing monoclonal antibodies (McAb) originated in 1975 and had great effects on fundamental research in biology and medical science, as well as in the diagnosis and therapy of diseases. Along with the extensive application of monoclonal antibodies in clinical therapy, however, it has been found that use of murine monoclonal antibody agents in humans leads to the appearance of human anti-mouse antibodies (HAMA); the molecular weight of the antibody is so great that it makes the amount of antibody available in the target site inadequate; which leads to low efficacy of the antibodies per se, and makes the curative effects unsatisfactory. To overcome these defects, humanization of the antibody is carried out, such processes have been developed from studies on preparation of human-mouse chimeric antibodies, preparation of antibody fragments of small molecules such as single chain antibodies and preparation of bifunctional antibodies. For example, 7E3, a murine monoclonal antibody against GPIIb-IIIa, was prepared by American researchers in 1983. (Coller B S, Peerschke E I, Scudder L E et al. A murine monoclonal antibody that completely blocks the binding of fibrinogen to platelets produces a thrombasthenic-like state in normal platelets and binds to glycoprotein IIb/IIIa. *Journal of Clinical Investigation.* 1983; 72(1): 325–328). In 1992, it was reconstructed as the Fab fragment of the human-mouse chimeric antibody named c7E3. (Knight D M, Wagner C, Jordan R, et al. The immunogenicity of the 7E3 murine Fab monoclonal-antibody fragment variable region is dramatically reduced in humans by substitution of human for murine constant regions. *Molecular Immunology.* 1995; 32 (16): 1271–1281). Large-scale clinical investigation has uncovered the fact that c7E3 has strong anti-thrombotic effects. The application of this Fab fragment in clinic practice has been approved by the FDA. Nowadays it is widely used in the treatment of ischemic heart disease and has shown that there is a favorable future for clinical application of these kinds of drugs.

However, a deficiency of c7E3 is in that it only acts on one epitope on the platelet membrane and blocks the function of the receptor in a single way and thus cannot achieve complete inhibition of platelet aggregation. So it is desirable to develop a novel monoclonal antibody, which can inhibit platelet aggregation more efficiently and effectively.

SUMMARY OF THE INVENTION

The present invention provides a dual specific antibody consisting of antibodies respectively acting on different sites on the platelet GPIIb-IIIa complex. The dual specific antibody of the present invention can completely block receptor function of the GPIIb-IIIa complex, inhibit platelet aggregation and thereby efficiently inhibit thrombosis. As a result, the dual specific antibody of the present invention, as a novel platelet GPIIb-IIIa receptor blocker, has incomparable advantages and prospective applicative value over conventional anti-platelet agents.

The first aspect of the invention is to provide novel monoclonal antibodies against a specific epitope of platelet membrane glycoproteins.

The second aspect of the invention is to provide novel hybridoma cells capable of producing monoclonal antibodies against a specific epitope of platelet membrane glycoproteins.

The third aspect of the invention is to provide a novel method for preparation of the monoclonal antibodies against a specific epitope of platelet membrane glycoproteins.

The fourth aspect of the invention is to provide novel monoclonal antibody fragments against a specific epitope of platelet membrane glycoproteins.

The fifth aspect of the invention is to provide a novel pharmaceutical composition capable of inhibiting platelet aggregation efficiently.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 3 shows the results of Western-blot analysis of monoclonal antibodies R813 and Y262.

DETAILED DESCRIPTION

Figure 1:
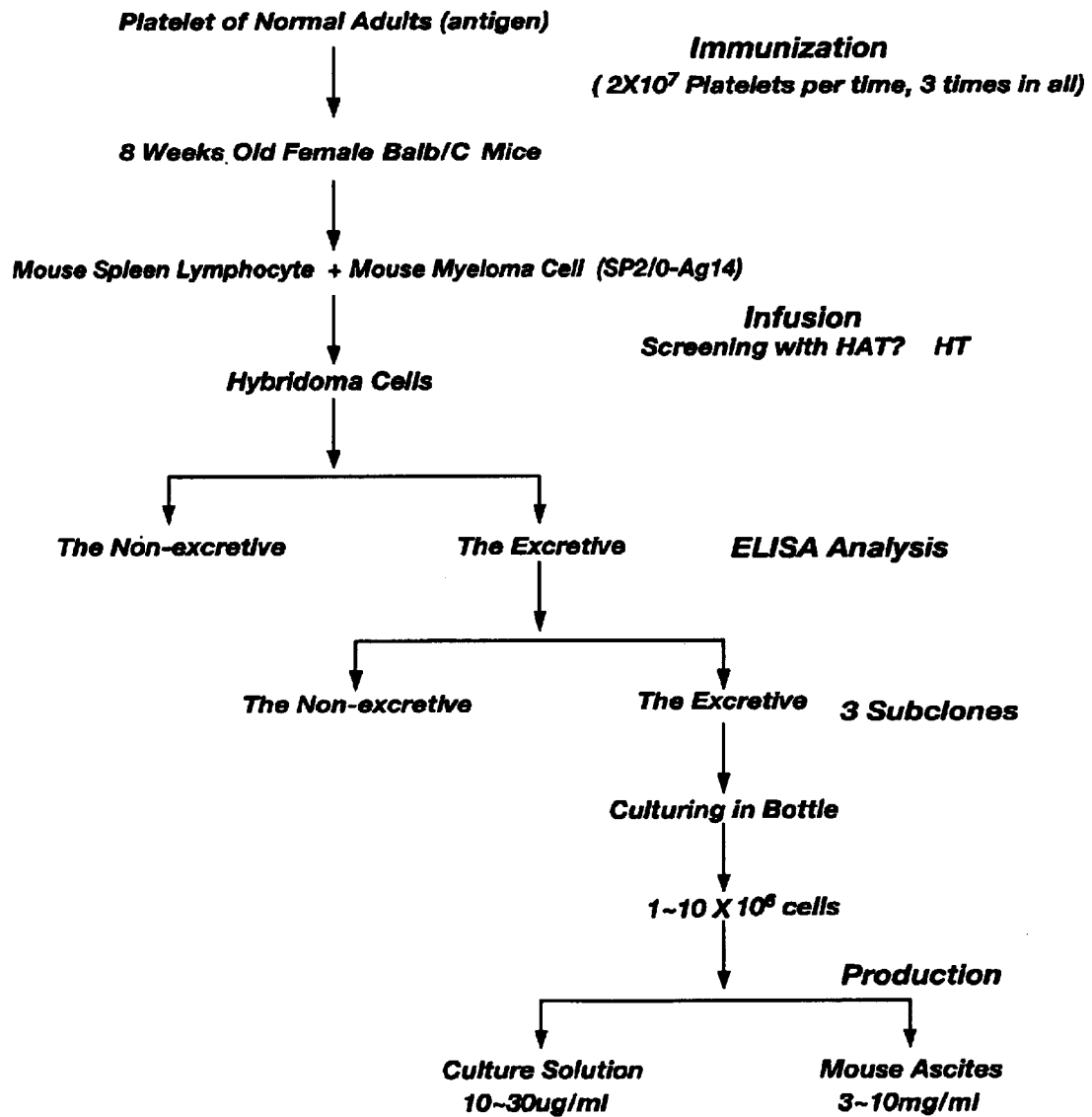
FIG. 1 shows the flow chart of preparation of hybridoma cells which excretes the monoclonal antibodies R813 and Y262.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

According to the first aspect of this invention, novel monoclonal antibodies against a specific epitope on the platelet membrane glycoprotein are provided.

A human platelet is adopted to immunize Balb/C mice and a number of monoclonal antibodies (about 20) against platelet GPIIIa or the GPIIb-IIIa complex are obtained. After repeated screening and testing, the monoclonal antibodies Y262, Y321, Y474 and R813 have been found to be capable of efficaciously inhibiting platelet aggregation. By means of a competitive radioimmunoassay of $^{125}I$ labeled monoclonal antibodies and the add-up of the mean intensity of fluorescence in flowcytometry, it was found that the epitopes recognized by the monoclonal antibodies of the invention are different, wherein the first group of monoclonal antibodies recognizing platelet GPIIIa are selected from R813, Y88, Y128 and Y474, the second group of monoclonal antibodies recognizing the platelet GPIIb-IIIa complex are selected from Y8, Y262, Y291, Y295, Y321, Y342, Y458, Y585 and Y700. The preferred monoclonal antibody from the first group is R813 and that of the second group is Y262.

According to the second aspect of the invention, novel hybridoma cell lines capable of producing monoclonal antibodies against a specific epitope of platelet membrane glycoproteins are provided. Particularly, the invention provides hybridoma cell lines capable of producing the above monoclonal antibodies of the first and second groups, respectively, which are selected from hybridoma cells R813, Y88, Y128 and Y474 that produce monoclonal antibodies recognizing platelet GPIIIa, and hybridoma cells Y8, Y262, Y291, Y295, Y321, Y342, Y458, Y585 and Y700 that produce monoclonal antibodies recognizing the platelet GPIIb-IIIa complex, wherein the preferred hybridoma cells are R813 and Y262. The two hybridoma cells were deposited on Apr. 30, 2002 with the China General Microbiological Culture Collection Center(CGMCC) (Address: Institure of Microbiology, Chinese Academy of Science, P.O.Box 2714, Beijing 100080, China), an International Deposition Authority under the Budapest treaty, having the accession numbers of CGMCC No. 0740 and CGMCC No. 0741 respectively.

According to the third aspect of this invention, a novel method for preparing the monoclonal antibodies against specific epitopes on platelet membrane glycoproteins is provided. Said method includes using human platelets as an immunogen to immunize Balb/C mice, fusing the spleen cells of the immunized mice with the myeloma cells-SP2/0-Ag14 to prepare hybridoma cells capable of producing monoclonal antibodies recognizing platelet GPIIIa or GPIIb-IIIa complexes, identifying the epitopes of the monoclonal antibodies by means of ELISA, FCM, Western-blot and affinity chromatography, investigating the binding activity of monoclonal antibodies to platelets and purifying the monoclonal antibodies.

According to the fourth aspect of this invention, novel F(ab')$_2$ fragments of monoclonal antibodies against specific epitopes on platelet membrane glycoproteins, are provided. Papain is used to digest the monoclonal antibodies R813 and Y262 to prepare the F(ab')$_2$ fragments. After identifying the fragments with SDS-PAGE, the inhibition activities of the fragments and their "cocktail" are investigated.

According to the fifth aspect of this invention, a novel pharmaceutical composition that efficiently inhibits platelet aggregation is provided, comprising one or more of the monoclonal antibodies of this invention and if required, pharmaceutically acceptable carriers or adjuvants.

In a preferred embodiment of this invention, the monoclonal antibodies R813 and Y262, recognizing different epitopes, are screened by a competitive radioimmunoassay of $^{125}I$ labeled monoclonal antibody and calculation of mean intensity of fluorescence in flowcytometery. Combined use of R813 and Y262 is found to completely inhibit platelet aggregation induced by ADP which allows a low dose of antibody to be used (the gross concentration is about 6–7 $\mu g/ml$). The experimental results indicate that R813 and Y262 act on different sites of the platelet GPIIb-IIIa complex and the "cocktail" of these two antibodies completely blocks the binding of fibrinogen to the platelet GPIIIb-IIIa receptor and thus inhibits platelet aggregation. Additionally, the F(ab')$_2$ fragments of these two monoclonal antibodies still inhibit platelet aggregation completely, the biological activities of which exceed that of c7E3 (tradename is Reopro). The applicants believe that this is the first time to a "cocktail" of two monoclonal antibodies has been used to block the receptor function of platelet membrane GPIIb-IIIa. Reopro acts on only one epitope of the platelet GPIIb-IIIa complex, blocks the receptor in a single way and the dose needed to achieve 50% inhibition of platelet aggregation is 5.5 $\mu g/ml$. Since the "cocktail" composition of the two monoclonal antibodies of the present invention acts on two different epitopes of the platelet GPIIb-IIIa complex sterically and completely inhibits fibrinogen completely from binding with its receptor, the dose for 50% inhibition is only 3.3 μg/ml. The "cocktail" composition of the two monoclonal antibodies of the present invention not only substantially decreases the dosage of monoclonal antibody used but also greatly increases the inhibition of platelet aggregation, i.e., the bioactivity exceeds that of Reorpo (c7E3). To alleviate the HAMA reaction induced by the monoclonal antibodies, and to reduce the molecular weight and increase the antibody concentration at the target site, the monoclonal antibodies R813 and Y262 are reconstructed by enzymolysis to prepare F(ab')$_2$ fragments. There are studies showing that the HAMA reaction from F(ab')$_2$ fragment of murine monoclonal antibody is no more severe than that from chimeric antibody and they have excellent affinity thus can be used directly. In vitro studies have shown that combined use of the F(ab')$_2$ fragments of these two antibodies is still capable of completely blocking the function of the platelet GPIIb-IIIa receptor and inhibiting platelet aggregation.

The present invention provides the monoclonal antibodies R813 and Y262 that act on different epitopes of the platelet GPIIb-IIIa complex and inhibit platelet aggregation more efficiently. The "cocktail" composition of the two antibodies of the present invention is capable of completely blocking the platelet GPIIb-IIIa receptor and inhibiting platelet aggregation. The biological activity of the "cocktail" composition of the two antibodies of the present invention exceeds that of Reopro, a well-known anti-platelet agent, and allows a low dose to be used. The F(ab')$_2$ fragments prepared by enzymolysis of the monoclonal antibodies of the present invention retain their bioactivity, bring down the molecular weight of the antibodies, and leads to availability of more antibody at the target site. Removal of the Fc fragment decreases the HAMA reaction and reduces damage from platelets induced by binding with the reticuloendothelial system. In addition, enzymolysis is simple to operate and is low in cost. In view of the above-mentioned potent and efficient bioactivity, low cost and simplicity of operation, the present invention exhibits tremendous anti-thrombotic potential and has excellent marketing prospects.

The following Examples are provided to further aid in understanding the invention, and pre-suppose an understanding of conventional methods well-known to those persons having ordinary skill in the art to which the examples pertain. The particular materials and conditions described hereunder are intended to exemplify particular aspects of the invention and should not be construed to limit the reasonable scope thereof.

EXAMPLE 1

Preparation of Hybridoma Cells that Produce Monoclonal Antibodies R813 and Y262

1.1 Material:

Balb/C mice were purchased from Charles River Laboratories Inc. Canada., SP2/0-Ag14 mouse myeloma cells, myelocytoma cells (K562), acute lymphosarcoleukemia cells (MOLF-4) and acute T-cell leukemia cells of human origin(Jurkat E-6) were purchased from ATCC Inc. USA, D-MEM/F$_{12}$, RMPI1640, L-Glutamine, MEM non-essential, HT Supplement, HAT Supplement, Antibiotic-Antimycotic were all purchased from GIBCO Inc. 8-Azaguanie was purchased from Sigma. 50% PEG 1500 Solution was purchased from ROCH Inc. A Subclass Identification of Mouse IgG Kit was purchased from Biorad Inc. Other reagents were purchased from domestic companies.

1.2 Methods:

Platelets were extracted from anticoagulated normal human whole blood, washed with TEN 3 times, suspended with PBS and the platelet concentration was adjusted to $1 \times 10^8$ cell/ml, then 0.2 ml of platelets were injected into the abdominal cavity of 8 week old female Balb/C mice. After 4 weeks this operation was repeated, another 4 weeks later 0.2 ml of platelet suspension was injected into the tail veins, and 3 days later the mice were sacrificed. The spleen was taken out for preparation of a spleen cell suspension. $10^8$ spleen cells were fused with $10^7$ SP2/0-Ag 14 cells in their logarithmic growth phase in accordance with conventional methods. The cells were cultivated with HAT supplement and HT supplement in turn each for 2 weeks were then changed to a common complete media. During this period the cell clones were detected with ELISA using platelet coated immunoassay plates and more than 20 hybridoma cell clones were found to have remarkable binding reactivity with platelets. Subcloning of these positive and selected hybridoma cell clones was done three times according to a limiting dilution method and the clones were transferred to a 24-well cultivating plate and bottle, and mouse ascites was prepared (FIG. 1). 12 cell strains obtained as above, which steadily secrete anti-platelet monoclonal antibodies, are R813, Y8, Y88, Y128, Y262, Y295, Y291, Y321, Y342, Y458, Y474, Y585 and Y700. Investigation of reactions between these antibodies and human red blood cells, white blood cells, K562, MOLF-4 and Jurkat E6-1cells by flow cytometry showed that all antibodies had no cross-linked reactivity with these cells. Besides, karyotype analysis of cells producing these antibodies indicated that they were all hybridoma cells. With the subclass identification kit (Biorad) it was found that the monoclonal antibodies R813, Y128, Y321, Y458, Y474, Y585 and Y700 belong to the IgG$_1$, Kappa subclass, Y8 and Y295 belong to the IgG$_{2a}$, Kappa subclass, Y88, Y262 and Y291 belong to the IgG$_{2b}$, Kappa subclass. Observation of the preferred hybridoma cells R813 and Y262 for several years demonstrated the capability of these two cell strains to steadily secrete monoclonal antibody of high valence. Therefore, productive cell libraries of these two cell strains were constructed.

EXAMPLE 2

Preparation and Purification of Monoclonal Antibodies R813 and Y262

2.1 Material:

Pristane was purchased from Sigma Inc., Balb/C mice were purchased from Shanghai Experimental Animal Research Center, a Protein G affinity chromatography column (1.0 ml, ready for use) was purchased from Pharmacia Inc. Other analytical reagents were purchased from domestic companies.

Figure 2:
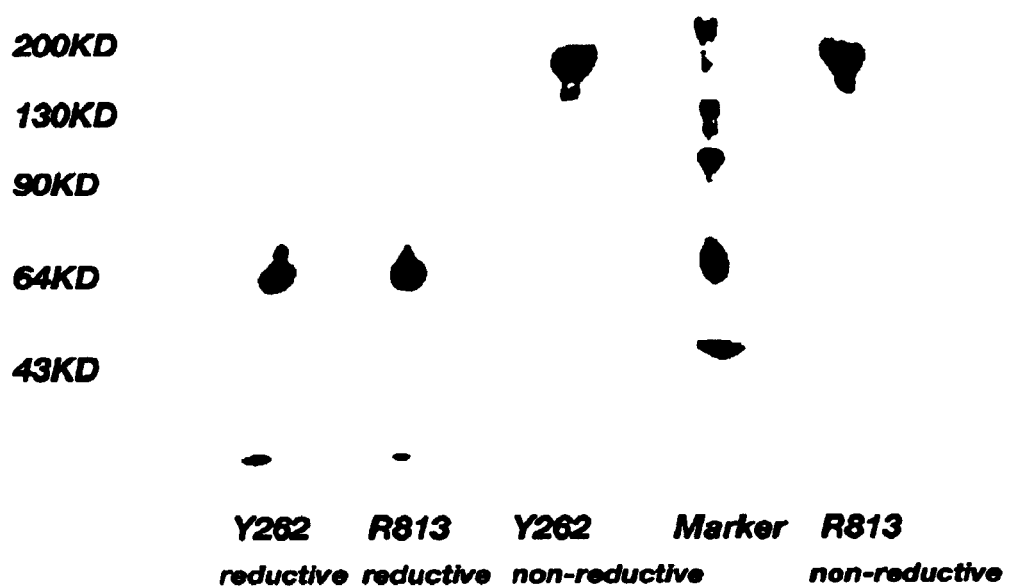
FIG. 2 shows the results of electrophoretic analysis of purified monoclonal antibodies R813 and Y262 IgG.

2.2 Methods:

1 ml pristane was injected into the abdominal cavity of 10 week old male Balb/C mice to make them allergic, 1~2 weeks later, $1~10 \times 10^6$ R813 and Y262 hybridoma cells were respectively injected into the abdominal cavity of the allergen-challenged mice, around a week later ascites formed and was collected. The ascetic fluid was then dialyzed against a 0.02 M PB solution (PH7.0) at 4□ over night, after centrifugation at 10000 rpm for 15 minutes at 4□ to remove precipitates and subsequent filtration with a 0.2 μm filter, the filtrate was applied to a protein G column 1 ml at a time, 0.02 M PB solution (pH7.0) was used to equilibrate the column and wash away any unneeded protein, followed by elution of the IgG with a 0.1 M Gly-HCl solution at a pH of 2.7. The eluate was collected and dialyzed against PBS, then after condensation and quantification, the eluate was identified with 10% SDS-PAGE. The results show the concentration of antibody in the ascite fluid was 8 mg/ml and the purity of the antibodies was above 90% (FIG. 2).

EXAMPLE 3

The Study on the Binding Activity of Monoclonal Antibodies R813 and Y262 with Platelets 3.1 Material:

Platelets were isolated from whole blood of normal adult donors, GAM-FITC was purchased from Huamei Inc. in Shanghai, GAM-HRP was purchased from Sigma Inc., CNBr-Sepharose 4B was purchased from Pharmacia Inc., a standard protein molecular weight marker was purchased from Sibasi Inc. in Shanghai, consisting of proteins with molecular weights of 43 KD, 66 KD, 97 KD, 130 KD and 200 KD, other reagents were purchased from domestic companies.

3.2 Methods:

(1) To study the binding activity of the monoclonal antibodies R813 and Y262 with platelets by ELISA: platelet rich plasma (PRP) was isolated from anticoagulated blood of healthy subjects, washed three times with TEN solution, the concentration was adjusted to $5 \times 10^5$/ml. 0.1 ml of platelets were dispensed into each well of the ELISA plate and the plate was placed at 4□ over night, followed by 2 hours of blocking at 37° C. with 2% BSA-PBS, immobilized with 0.5% glutaraldehyde, washed with 0.01% Tween 20-PBS, with GAM-HRP acting as a secondary antibody and the color was developed with an OPD, then the absorbance at 490 nm was tested by conventional ELISA. Mouse-IgG was used as the negative control and the antibody SZ-22 (against GPIIb) as the positive control. The results show the excellent binding activity of R813 and Y262 with platelets.

(2) to study the binding activity of the monoclonal antibodies R813 and Y262 with platelets by flowcytometry: 5 $\mu$l PRP (the platelet concentration is $5 \times 10^8$/ml) was mixed with 50 $\mu$l of asctic fluid containing the antibodies R813 and Y262 (1:100 diluted with PBS) respectively, the mixture was placed at room temperature for 30 minutes, after washing GAM-FITC was added, the specimens were tested with flowcytometry (Coulter EPICS$^R$, XL). Mouse-IgG was used as the negative control and equally diluted antibody SZ-22 as the positive control. The results show that the antibodies R813 and Y262 were capable of binding to platelets. (FIG. 5.)

(3) Determination of binding sites of antibodies R813 and Y262 with platelet membrane glycoproteins by Western-blot assay: PRP was extracted from EDTA-anticoagulated whole blood, washed three times with TEN solution and the platelet concentration was adjusted to $2 \times 10^8$/ml. The platelets were lysed when 1 mM PMSF and 1% TritonX-100 were added. After centrifugation, the supernatant was dispensed in plates in the amount of 60 $\mu$l/well, and non-reductive SDS-PAGE was carried out under a 5%–15% logarithmic gradient, then the protein was transferred onto a nitrocellulose membrane. After blocking with 2% BSA-PBS, the membrane was cut into strips and incubated respectively with the antibodies R813 and Y262 at 37° C. for 2 hours with GAM-HRP as the secondary antibody. Finally chloronaphthalenephenol was added to develop color. Mouse-IgG was used as the negative control and antibody SZ-22 as the positive control. The results show that R813 acted on platelet GPIIIa, while no reaction took place with Y262. (FIG. 3.)

Figure 4:
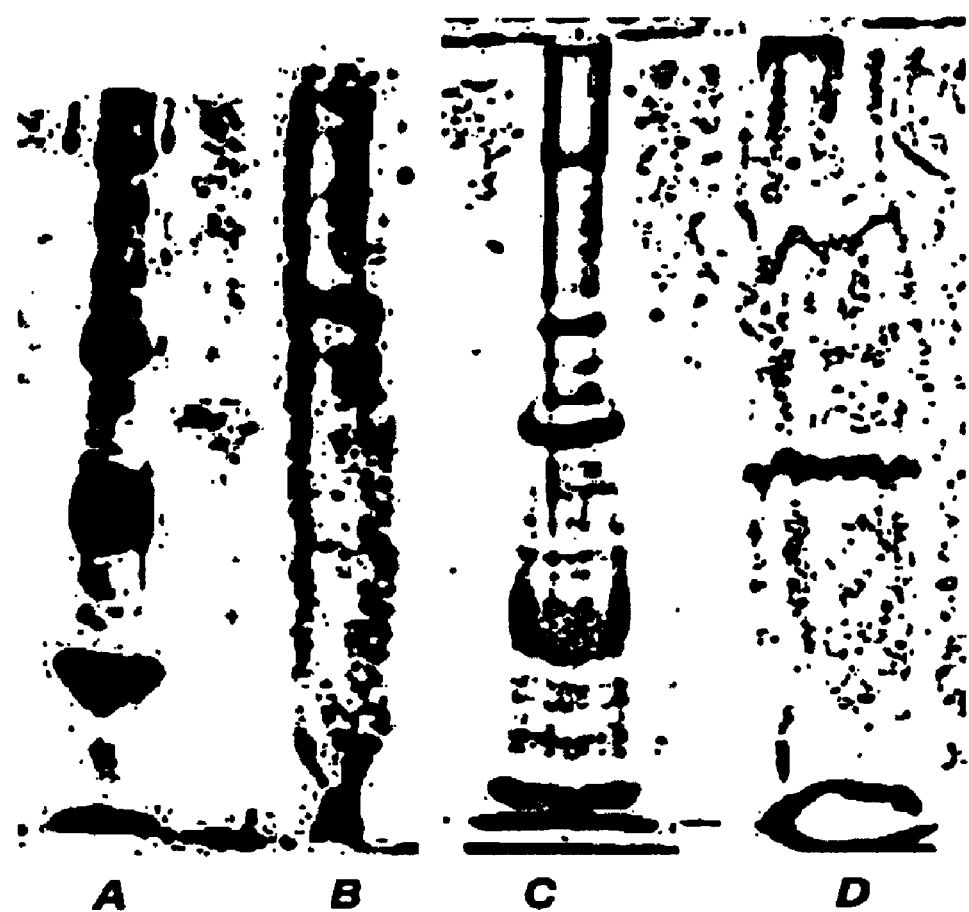
FIG. 4 shows the results of electrophoretic analysis of the product obtained by affinity chromatography linked with R813 and Y262, wherein A represents a protein marker; B represents the non-reductive product of R813; C represents a protein marker; D represents the non-reductive product of Y262.
Figure 5A:
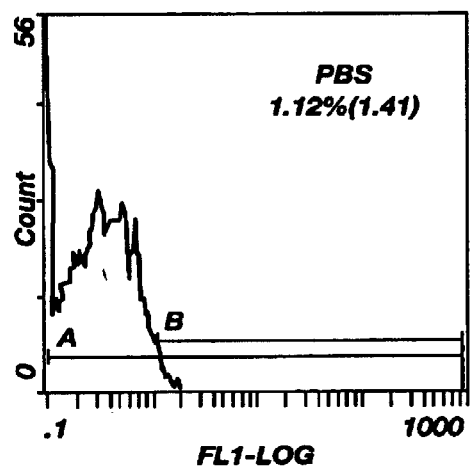
FIG. 5 shows the binding activity of monoclonal antibodies R813, Y262 to platelets, wherein A represents the negative control; B represents the positive control, SZ-22; C represents the monoclonal antibody R813 and D represents the monoclonal antibody Y262.
Figure 5B:
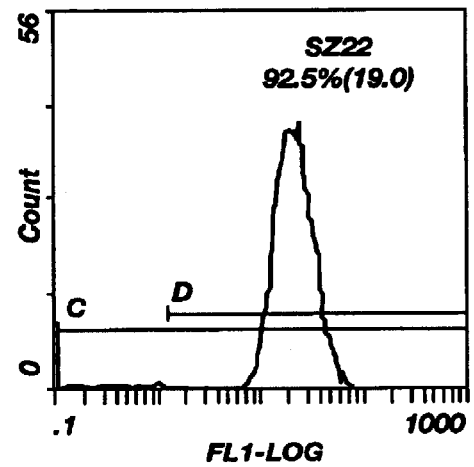
Figure 5C:
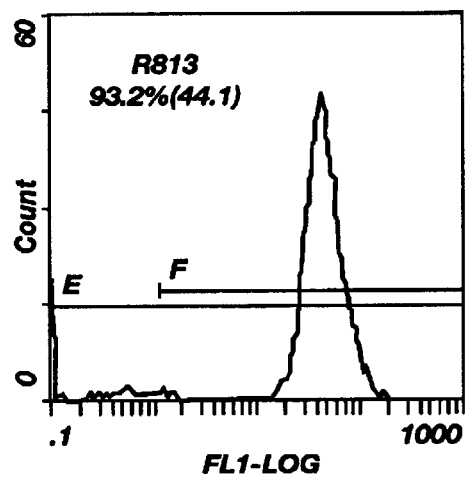
Figure 5D:
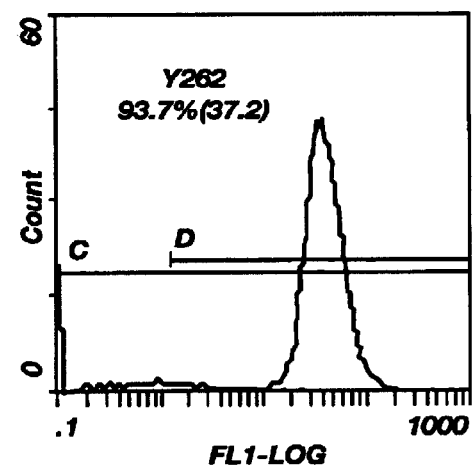

(4) Determination of the binding sites of the antibodies R813 and Y262 with platelet membrane glycoproteins by affinity chromatography: CNBr-Sepharose 4B gel was soaked with 1 mM HCl for 4 hours then washed three times with coupling buffer. Purified antibodies R813 and Y262 were sufficiently dialyzed and then applied to the prepared gel respectively. The mixture was vibrated for 16 hours at 4° C., after which it was washed with coupling buffer in tundish, saturated with 1 mM ethanolamine twice, each time for one hour, then washed with coupling buffer, 25 mM Tris-HCl and TBS in turn, and lastly it was loaded into the column. The platelet lysate was prepared according to method (3). The lysate consisting of $2 \times 10^9$ platelets was applied to the column repeatedly and eluted with 0.05M diethyl amine-5 mM EDTA buffer. The eluate was dialyzed against PBS and after being concentrated it was identified with 10% SDS-PAGE. The results show that R813 recognized platelet GPIIIa, while Y262 recognized the platelet GPIIb-IIIa complex (FIG. 4.)

EXAMPLE 4

Different Epitopes of the Platelet GPIIb-IIIa Receptor that the Antibodies R813 and Y262, Respectively, Recognize 4.1 Material:

$^{125}$I was purchased from China Nuclear Power Company, Sephadex G-25 gel was purchased from Pharmacia Inc., other reagents were all analytical reagents purchased from domestic companies.

Figure 6:
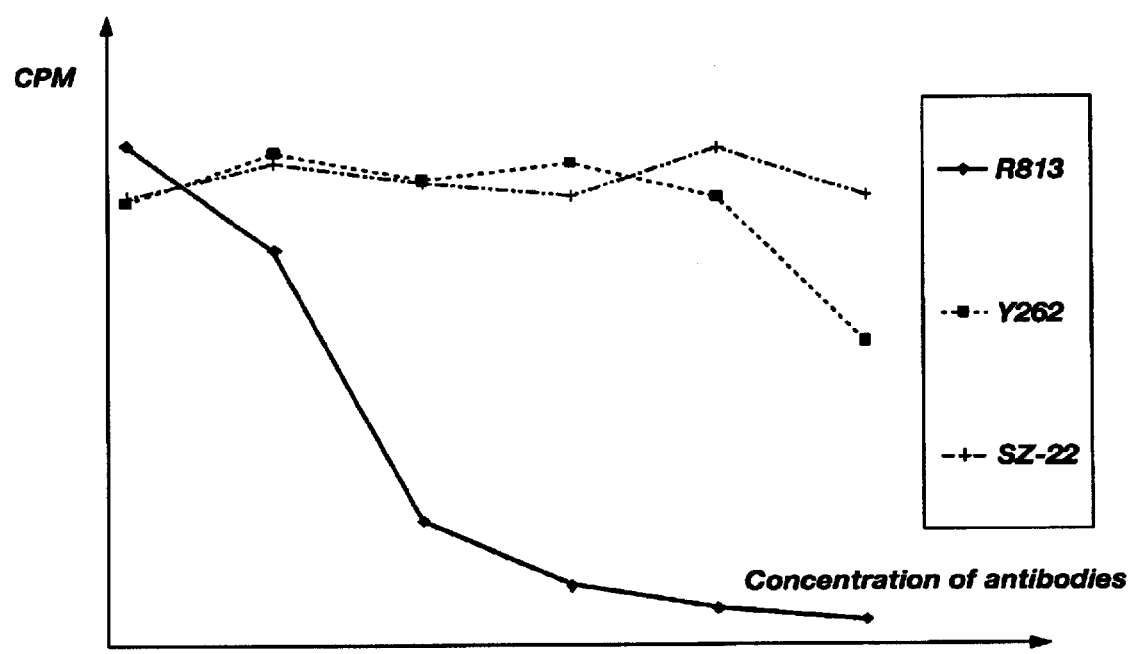
FIG. 6 shows the results of a radioimmuno assay competitive inhibition experiment of $^{125}I$ labeled monoclonal antibodies Y262 and R813.

4.2 Methods:

Competitive radioimmunoassay of $^{125}$I labeled monoclonal antibody R813: 30 $\mu$g of R813 (1 mg/ml) was mixed with 10 $\mu$l 0.1M PB pH 7.5, 1 mGi $^{125}$I and 10 $\mu$l ChT (5 mg/ml), the mixture was placed at room temperature for 1 minute, then 20 $\mu$l $Na_2S_2O_8$ (20 mg/ml) was added and placed at room temperature for another minute, the reaction was ended with the addition of 100 $\mu$l 0.5% BSA-PBS. The reaction mixture was applied to a Sephadex G-25 gel column pre-equilibrated with 0.5% BSA-PBS, and eluted with the same solution. The eluate was collected in the amount of 10 drops per vial. Then the radioactivity of each vial was tested with a $\gamma$ counter and the vial having the first radioactive peak was collected. Platelets were coated on an ELISA plate according to the previous method. A fixed amount of $^{125}$I-R813 was mixed with different concentrations of murine IgG, R813 and Y262, respectively, after that the mixtures were dispensed into the ELISA plate, followed by 2 hours of incubation at 37° C. and washing three times. The radioactivity was tested with a $\gamma$ counter. The negative control was mouse IgG. The results show that the radioactivity dropped with an increase in the concentration of R813, while it remained unchanged as the concentrations of Y262 and murine IgG varied, which indicates that R813 and Y262 recognize different epitopes (FIG. 6.)

EXAMPLE 5

The Synergetic Action of the Antibodies R813 and Y262 in Blocking the Platelet GPIIb-IIIa Complex and in Inhibiting Platelet Aggregation 5.1 Material:

ADP was purchased from Lizhudongfeng Biological Product Inc. Shanghai, GAM-FITC was purchased in Huamei Inc. Shanghai. Other reagents were all analytical reagents purchased from domestic companies.

5.2 Methods:

(1) The add-up of mean intensity of fluorescence by flow cytometry: 5 $\mu$l PRP was mixed with R813, Y262, and a mixture of both, respectively, and placed at room temperature for 30 minutes. GAM-FITC was added after washing, then the mixture was detected with a flowcytometer. Mouse IgG was used as the negative control. The results show that the mean intensity of fluorescence of a combination of R813 and Y262 corresponded to the sum of that of the two individual antibodies, which indicates that the two antibodies can simultaneously act on their respective epitopes, and thus synergetically block the platelet GPIIb-IIIa complex. (Table 1.)

TABLE 1

The add-up of mean fluorescent intensity of R813 and Y262 by flow cytometry

| Antibody | Percentage of positive cell (%) | Mean fluorescent intensity |
|---|---|---|
| PBS | 3.22 | 2.61 |
| M-IgG | 6.48 | 3.26 |
| SZ-22 | 90.2 | 83.1 |
| R813 | 87.7 | 185.7 |
| Y262 | 73.6 | 130.9 |
| R813 + M-IgG | 86.4 | 174.8 |
| R813 + SZ-22 | 92.3 | 255.4 |
| R813 + R813 | 87.6 | 180.1 |
| R813 + Y262 | 88.1 | 338.5 |

(2) The synergetic action of antibodies R813 and Y262 in inhibiting platelet aggregation induced by ADP: PRP was prepared from citrate-anticoagulated whole blood of healthy adults, then 200 μl PRP was mixed with R813, Y262, and a mixture of both respectively, after being incubated at 37° C. for 5 minutes ADP was added (final concentration was 5 uM) and the aggregation rate induced was tested. Mouse IgG was used as the negative control and Reopro as the positive control. The results show that R813 and Y262 inhibit platelet aggregation efficiently, and combined use of both under the same concentrations exhibited enhanced inhibition, platelet aggregation thus can be completely blocked, its anti-thrombotic activity was superior to that of Reopro. The dose needed for 50% inhibition was found to be less than that of Reopro. (Table 2. 3. and 4.)

TABLE 2

The Effect of different concentrations of antibodies on platelet aggregation

First Experiment

| | | Monoclonal antibody | | | | | |
|---|---|---|---|---|---|---|---|
| Experiment times | Control | R813 | | Y262 | | 7E3 | |
| Concentration (μg/ml) | PBS 0 | 2.5 | 5.0 | 2.5 | 5.0 | 2.5 | 5.0 |
| | | Platelet aggregation rate (%) | | | | | |
| 1 | 82% | 63% | 74% | 69% | 75% | 69% | 37% |
| 2 | 86% | 75% | 46% | 81% | 65% | 53% | 22% |
| Mean | 84% | 69% | 60% | 75% | 70% | 61% | 29.5% |

Second Experiment

| | | Monoclonal antibody | | | | | |
|---|---|---|---|---|---|---|---|
| Experiment times | Control | R813 | | Y262 | | 7E3 | |
| Concentration (μg/ml) | PBS 0 | 5.0 | 10.0 | 5.0 | 10.0 | 5.0 | 10.0 |
| | | Platelet aggregation rate (%) | | | | | |
| Mean | 59% | 53% | 22% | 64% | 28% | 47% | 43% |

Third Experiment

| | | Monoclonal antibody | | | |
|---|---|---|---|---|---|
| Experiment times | Control | R813 | | Y262 | |
| Concentration (μg/ml) | PBS 0 | 5.0 | 10.0 | 5.0 | 10.0 |
| | | Platelet aggregation rate (%) | | | |
| 1 | 61% | 60% | 23% | 67% | 54% |
| 2 | 72% | 68% | 40% | 58% | 52% |
| Mean | 66.5% | 64% | 31.5% | 62.5% | 53.5% |

TABLE 3

The Effect of R813, Y262 and the "Cocktail" thereof (DiMab) on platelet aggregation First Experiment

| | | Monoclonal antibody | | |
|---|---|---|---|---|
| Experiment times | Control | DiMab | R813 | Y262 |
| Concentration (μg/ml) | PBS 0 | 10.0 | 10.0 | 10.0 |
| | | Platelet aggregation rate (%) | | |
| 1 | 73% | 0% | 42% | 62% |
| 2 | 77% | 0% | 51% | 54% |
| Mean | 75% | 0% | 46.5% | 58% |

Second Experiment

| | | Monoclonal antibody DiMab | | | | |
|---|---|---|---|---|---|---|
| Experiment times | Control | | | | | |
| Concentration (μg/ml) | PBS 0 | 0.625 | 1.25 | 2.5 | 5.0 | 10.0 |
| | | Platelet aggregation rate (%) | | | | |
| 1 | 62% | 67% | 55% | 61% | 30% | 4% |
| 2 | 74% | 70% | 63% | 61% | 17% | 5% |
| 3 | 67% | 88% | 66% | 58% | 25% | 7% |
| Mean | 67.7% | 75% | 61.3% | 60% | 24% | 5.3% |

Third Experiment

| | | Monoclonal antibody | | | | | |
|---|---|---|---|---|---|---|---|
| Experiment times | Control | DiMab | | | 7E3 | | |
| Concentration | PBS | 1.25 | 2.50 | 5.0 | 10.0 | 1.25 | 2.50 | 5.0 | 10.0 |

TABLE 3-continued

The Effect of R813, Y262 and the "Cocktail" thereof (DiMab) on platelet aggregation

| (μg/ml) | 0 | Platelet aggregation rate (%) | | | | | | | |
|---|---|---|---|---|---|---|---|---|---|
| 1 | 44% | 30% | 19% | 14% | 0% | 54% | 35% | 23% | 5% |
| 2 | 49% | 38% | 38% | 8% | 0% | 53% | 31% | 28% | 6% |
| Mean | 46.5% | 34% | 28.5% | 11% | 0% | 53.5% | 33% | 25.5% | 5.5% |

TABLE 4

50% effective dosage of "cocktail" (DiMab) and 7E3 for platelet aggregation

| | DiMab | 7E3 |
|---|---|---|
| μg/ml | 3.13 | 5.26 |

TABLE 5

Inhibition Effect of F(ab')$_2$ Fragments on Platelet Aggregation

| | 1.25 | 2.50 | 5.0 | 10.0 | 20.00 μg/ml |
|---|---|---|---|---|---|
| | Platelet Aggregation Inhibition Rate (%) | | | | |
| R813 | 16.2 | 11.8 | 76.5 | 82.4 | 94.1* |
| Y262 | 35.1 | 42.9 | 61.0 | 9.1 | 55.8 |
| DiMab | 17.5 | 17.5 | 81.3 | 100 | 100 |

EXAMPLE 6

The Preparation and Identification of F(ab')$_2$ Fragments of Antibodies R813 and Y262

6.1 Material:

Papain was purchased from Lizhudongfeng Biological Product Inc. Shanghai, DEAE-52 gel was purchased from Sibasi Inc. Biochemistry Research Institute, Shanghai, DTT was the product of Fluka Inc. Other reagents were all analytical reagents purchased from domestic companies.

Figure 7:
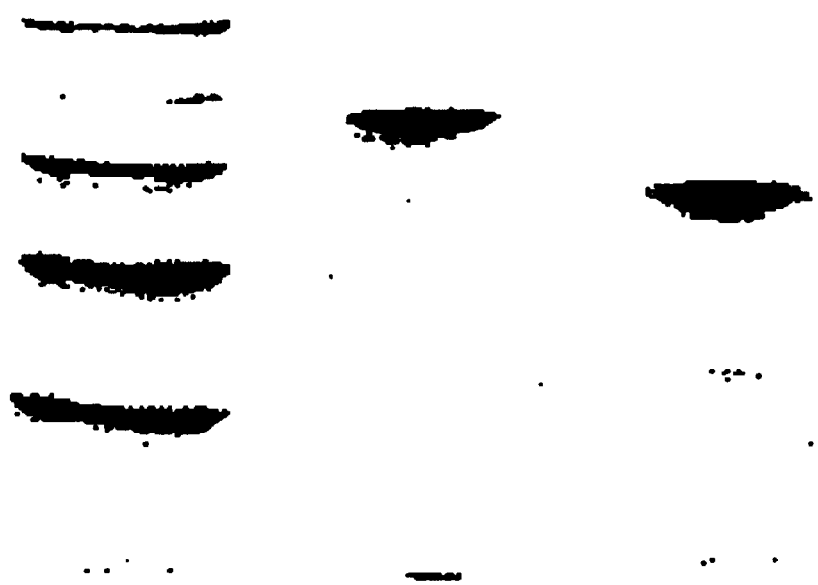
FIG. 7 shows the results of electrophoretic analysis of the F(ab')$_2$ fragments of the monoclonal antibodies R813 and Y262.

6.2 Methods:

(1) Preparation and identification of F(ab')$_2$ fragments of R816 and Y262: R813 and papain were mixed uniformly in a ratio of 5:1, and reacted at 4° C. for 24 hours, then the reaction was ended by addition of iodoacetamide (final concentration was 80 mM). The digested product was dialyzed against 0.01M Tris-HCl pH8.0 and was then applied to a DEAE-52 gel column. 0~0.3 M NaCl and 0.01M Tris-HCl PH8.0 were used as the eluents and the first eluted peak was collected. Y262 and papain were mixed uniformly in a ratio of 80:1, and reacted at 4° C. for 35 minutes. Then papain and Y262 in a ratio of 1:160 were added, and reacted at 4° C. for another 35 minutes. The subsequent process was the same as that used for R813 but the second eluted peak instead of the first was collected. The collected products were treated by reduced and non-reduced SDS-PAGE under a 10% gradient degree. The results show that the digested products were F(ab')$_2$ fragments of antibodies (FIG. 7.)

(2) Inhibition of platelet aggregation induced by ADP, by F(ab')$_2$ fragments of R813 and Y262: The method was the same as above and the results show that the F(ab')$_2$ fragments of R813 and Y262 still had the synergistic action of completely inhibiting platelet aggregation. (Table 5.)

It is to be understood that the above-referenced arrangements are illustrative of application of the principles of the present invention. Numerous modifications and alternative arrangements can be devised without departing from the spirit and scope of the present invention. While the present invention has been shown in the drawings and described above in connection with the exemplary embodiments(s) of the invention, it will be apparent to those of ordinary skill in the art that numerous modifications can be made without departing from the principles and concepts of the invention as set forth in the claims.

What is claimed is:

1. A pharmaceutical composition capable of efficiently inhibiting platelet aggregation comprising a combination of a whole or an antigen-binding fragment of a monoclonal antibody R813 obtained from a hybridoma CGMCC No. 0740 and a whole or an antigen-binding fragment of a monoclonal antibody Y262 obtained from hybridoma CGMCC No. 0741.

2. The pharmaceutical composition according to claim 1, wherein said monoclonal antibody R813 specifically recognizes GPIIIa located on platelet membranes.

3. The pharmaceutical composition according to claim 1, wherein said monoclonal antibody Y262 specifically recognizes GPIIb-IIIa complexes located on platelet membranes.

4. The pharmaceutical composition according to claim 1, wherein each of said fragments is an F(ab')$_2$ fragment.

5. The pharmaceutical composition according to claim 1, wherein said monoclonal antibody R813 and monoclonal antibody Y262 are present at a concentration ratio of 1:1.

6. The pharmaceutical composition according to claim 1, further comprising a pharmaceutically acceptable carrier or excipient.

7. A method for preventing platelet aggregation by administering the pharmaceutical composition according to claim 1.

* * * * *